United States Patent
Wendlandt et al.

(10) Patent No.: US 8,568,028 B2
(45) Date of Patent: Oct. 29, 2013

(54) MOBILE RADIOGRAPHY UNIT HAVING COLLAPSIBLE SUPPORT COLUMN

(75) Inventors: William C. Wendlandt, Rush, NY (US); James H. Ogle, Fairport, NY (US); James G. Coyne, Rochester, NY (US); Anthony DiRisio, Rochester, NY (US); Christopher J. Kralles, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 211 days.

(21) Appl. No.: 12/906,192

(22) Filed: Oct. 18, 2010

(65) Prior Publication Data

US 2011/0249804 A1 Oct. 13, 2011

Related U.S. Application Data

(60) Provisional application No. 61/323,503, filed on Apr. 13, 2010.

(51) Int. Cl.
 *H05G 1/02* (2006.01)
(52) U.S. Cl.
 USPC .................................. 378/198; 378/193
(58) Field of Classification Search
 USPC ................................ 378/193–198
 See application file for complete search history.

(56) References Cited

U.S. PATENT DOCUMENTS

| | | | |
|---|---|---|---|
| 2,041,242 A | 5/1936 | Goldfield | |
| 3,790,805 A * | 2/1974 | Foderaro | 378/198 |
| 4,341,279 A | 7/1982 | Waerve | 180/19 |
| 4,387,468 A | 6/1983 | Fenne et al. | |
| 4,716,581 A | 12/1987 | Barud | 378/198 |
| 5,067,145 A * | 11/1991 | Siczek et al. | 378/198 |
| 5,475,730 A | 12/1995 | Galando | 378/157 |
| 5,499,284 A | 3/1996 | Pellegrino et al. | 378/198 |
| 5,844,961 A | 12/1998 | McEvoy et al. | 378/98.8 |
| 6,193,415 B1 | 2/2001 | Kadowaki et al. | |
| 6,491,430 B1 | 12/2002 | Seissler | 378/207 |
| 6,851,853 B2 * | 2/2005 | Nakagawa et al. | 378/197 |
| 7,016,467 B2 | 3/2006 | Brooks | 378/102 |
| 7,211,802 B1 | 5/2007 | Dhurjaty et al. | 250/370.09 |
| 7,495,226 B2 | 2/2009 | Jadrich et al. | 250/370.09 |
| 7,611,282 B2 | 11/2009 | Koren et al. | 378/198 |

FOREIGN PATENT DOCUMENTS

| | | |
|---|---|---|
| JP | 04-164437 | 6/1992 |
| WO | 90-14748 | 11/1990 |

OTHER PUBLICATIONS

International Search Report & Written Opinion, International application No. PCT/US2011/032030, dated Dec. 19, 2011, 9 pages.

\* cited by examiner

*Primary Examiner* — Hoon Song

(57) ABSTRACT

A mobile radiography apparatus has a wheeled transport frame and a sectioned vertical column mounted on the frame, defining a vertical axis and having a base section with a first vertical position relative to the vertical axis and at least a first movable section that is translatable to a variable vertical position along the vertical axis. A boom apparatus supports an x-ray source, wherein the boom apparatus is coupled to the first movable section for positioning of the x-ray source along the vertical axis and extends outward with respect to the sectioned vertical column for positioning of the x-ray source in a direction that is orthogonal to the vertical axis.

21 Claims, 19 Drawing Sheets

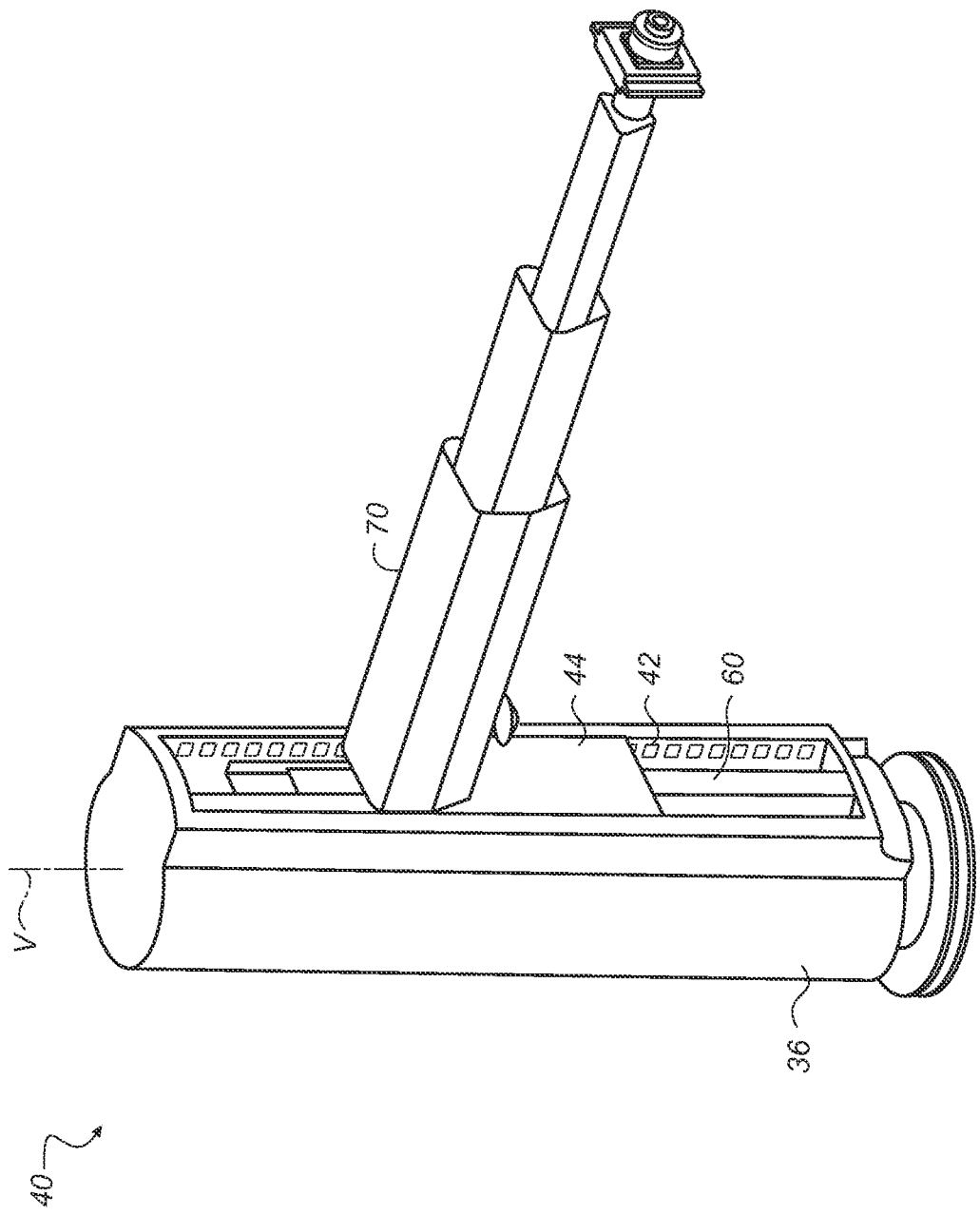

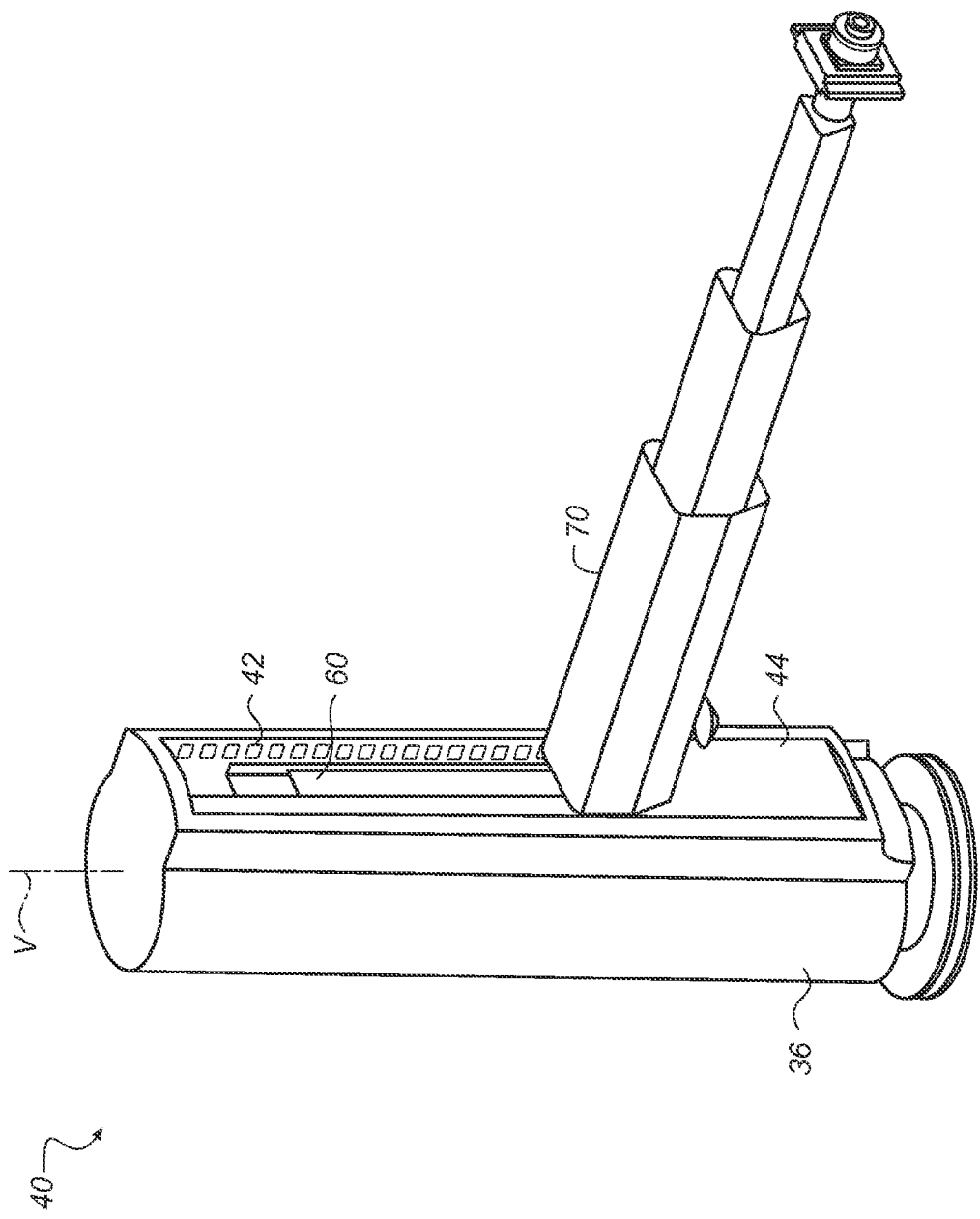

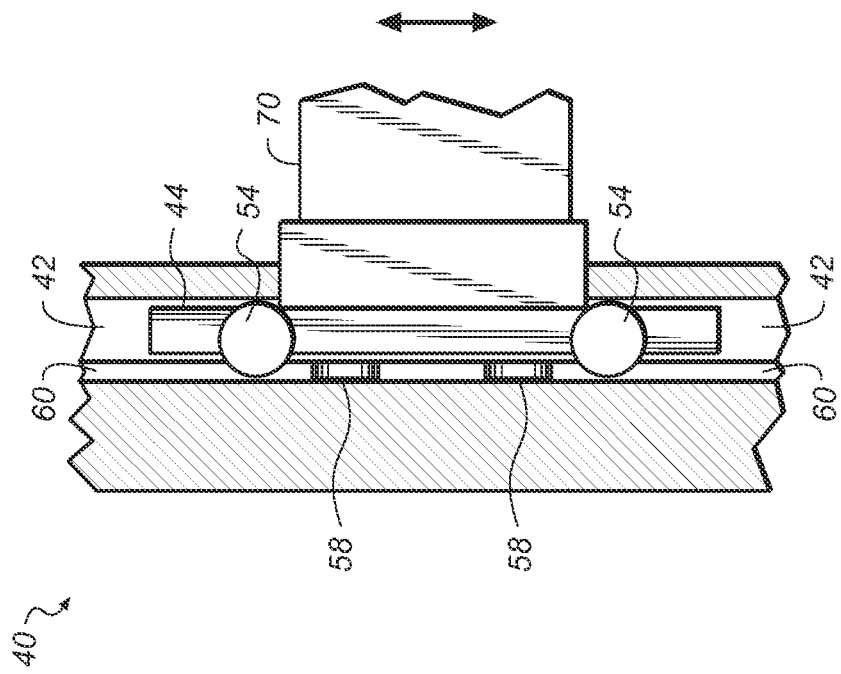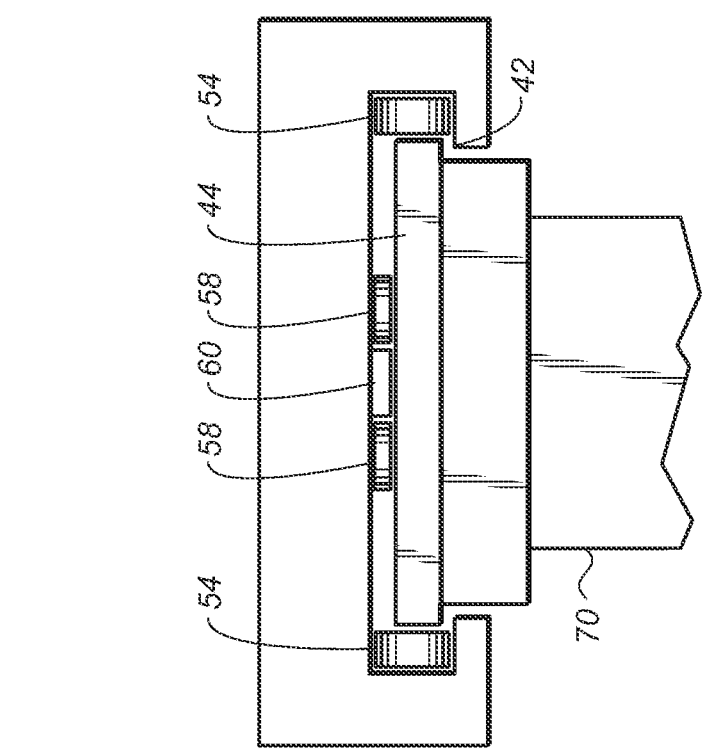

MOBILE RADIOGRAPHY UNIT HAVING COLLAPSIBLE SUPPORT COLUMN

CROSS REFERENCE TO RELATED APPLICATIONS

Reference is made to, and priority is claimed from, U.S. Ser. No. 61/323,503, filed as a provisional patent application on Apr. 13, 2010, entitled "MOBILE UNIT HAVING COLLAPSIBLE COLUMN", in the names of Ogle et al., and which is commonly assigned.

FIELD OF THE INVENTION

The present invention relates generally to the field of radiography and in particular to portable radiographic imaging apparatus. More specifically, the invention relates to a mobile radiography apparatus having a support column that is collapsible for enhanced mobility.

BACKGROUND

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

The perspective view of FIG. 1 shows an example of a conventional mobile x-ray apparatus that can be employed for computed radiography (CR) and/or digital radiography (DR). A mobile radiography unit 600 has a frame 620 that includes a display 610 for display of obtained images and related data and a control panel 612 that allows functions such as staring, transmitting, modifying, and printing of the obtained image.

For mobility, unit 600 has one or more wheels 615 and one or more handle grips 625, typically provided at waist-, arm-, or hand-level, that help to guide unit 600 to its intended location. A self-contained battery pack typically provides source power, eliminating the need for operation near a power outlet.

Mounted to frame 620 is a support member 635 that supports an x-ray source 640, also termed an x-ray tube, tube head, or generator mounted on a boom apparatus, more simply termed a boom 70. In the embodiment shown, support member 635 has a vertical column 64 of fixed height. Boom 70 extends outward a variable distance from support member 635 and rides up and down column 64 to the desired height for obtaining the image. Boom 70 may extend outward by a fixed distance or may be extendible over a variable distance. Height settings for the x-ray source 640 can range from low height for imaging feet and lower extremities to shoulder height and above for imaging the upper body portions of patients in various positions. In other conventional embodiments, the support member for the x-ray source is not a fixed column, but is rather an articulated member that bends at a joint mechanism to allow movement of the x-ray source over a range of vertical and horizontal positions.

One concern that must be addressed in design of the support member relates to ease of positioning of the x-ray source mounted on its boom. For ease of operation under varying conditions, the technician should be able to easily position and orient the x-ray source without requiring both hands, without the need of additional tools, and without needing help from nearby personnel. This includes moving the x-ray source from its clocked position used in transport to an imaging position. The mechanical problem of providing ease of positioning is complicated by the weight of the x-ray source and by its extension outward from the vertical axis.

While the conventional mobile x-ray apparatus described as unit 600 provides portable imaging capability in a number of applications, however, there are drawbacks to existing designs that can make these devices difficult to deploy in some circumstances. One of the problems common to conventional designs is due, in part, to the relative mobility and range of motion of the mobile x-ray apparatus that is needed.

The side view of FIG. 2 shows a significant problem that occurs when transporting a mobile radiography system, shown as a mobile radiography unit 62 that uses a fixed vertical structure, column 64. Boom 70 that provides transport of x-ray source 68, normally extended outward from unit 62 when in its imaging position, is folded hack toward a technician 66 for transport. This transport position helps to protect the x-ray source from damage or from causing an obstruction during movement. Column 64, however, obstructs the view of technician 66 when moving the unit from one place to another, so that objects that are near the front edge of unit 62 or directly in front of the unit cannot readily be seen. The technician is required to peer around the column during transport and can be more prone to colliding or bumping against other equipment or obstacles in the hospital ward or other location. The fixed vertical column 64 may also present difficulties when passing or moving alongside accessory equipment, furniture, or patient support equipment. With obstructed vision, the technician must move slowly, impacting productivity and response time. Accidents and mishaps are more likely.

Thus, there is a need for improvements in mobile x-ray apparatus design that allow these devices to be more easily transported and deployed.

SUMMARY OF THE INVENTION

An object of the present invention is to advance the art of mobile radiography. Another object of the present invention is to address the need for a mobile radiography unit that has the advantages of a vertical column but without the disadvantages of obstruction to operator visibility when wheeling the unit from one location to another.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

From one aspect, the present invention provides a mobile radiography apparatus comprising: a wheeled transport frame; a sectioned vertical column mounted on the frame and defining a vertical axis and comprising a base section having a first vertical position relative to the vertical axis and at least a first movable section that is translatable to a variable vertical position along the vertical axis; and a boom apparatus that supports an x-ray source, wherein the boom apparatus is coupled to the first movable section for positioning of the x-ray source along the vertical axis and extends outward with respect to the sectioned vertical column for positioning of the x-ray source in a direction that is orthogonal to the vertical axis.

From another aspect, the present invention provides a mobile radiography apparatus comprising: a wheeled transport frame; a sectioned vertical column mounted on the frame and defining a vertical axis and comprising a base section having a fixed vertical position relative to the vertical axis and at least a first movable section that is translatable to a variable vertical position along the vertical axis: a boom transport mechanism on the first movable section, wherein the boom transport mechanism is actuable to provide vertical movement along at least a portion of the first movable section; a boom apparatus coupled to the boom transport mechanism and extending outward with respect to the sectioned vertical column; and an x-ray source coupled to the boom apparatus for positioning using the boom transport mechanism.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 17 is a perspective view showing the boom transport on the upper section of the collapsible column, with the transport in a middle position.

FIG. 18 is a perspective view showing the boom transport on the upper section of the collapsible column, with the transport in a lower position.

FIG. 19A is a top view showing the carriage mechanism of the boom transport in one embodiment.

FIG. 19B is a top view showing the carriage mechanism of the boom transport in the FIG. 19A embodiment.

DETAILED DESCRIPTION OF THE INVENTION

Figure 1:
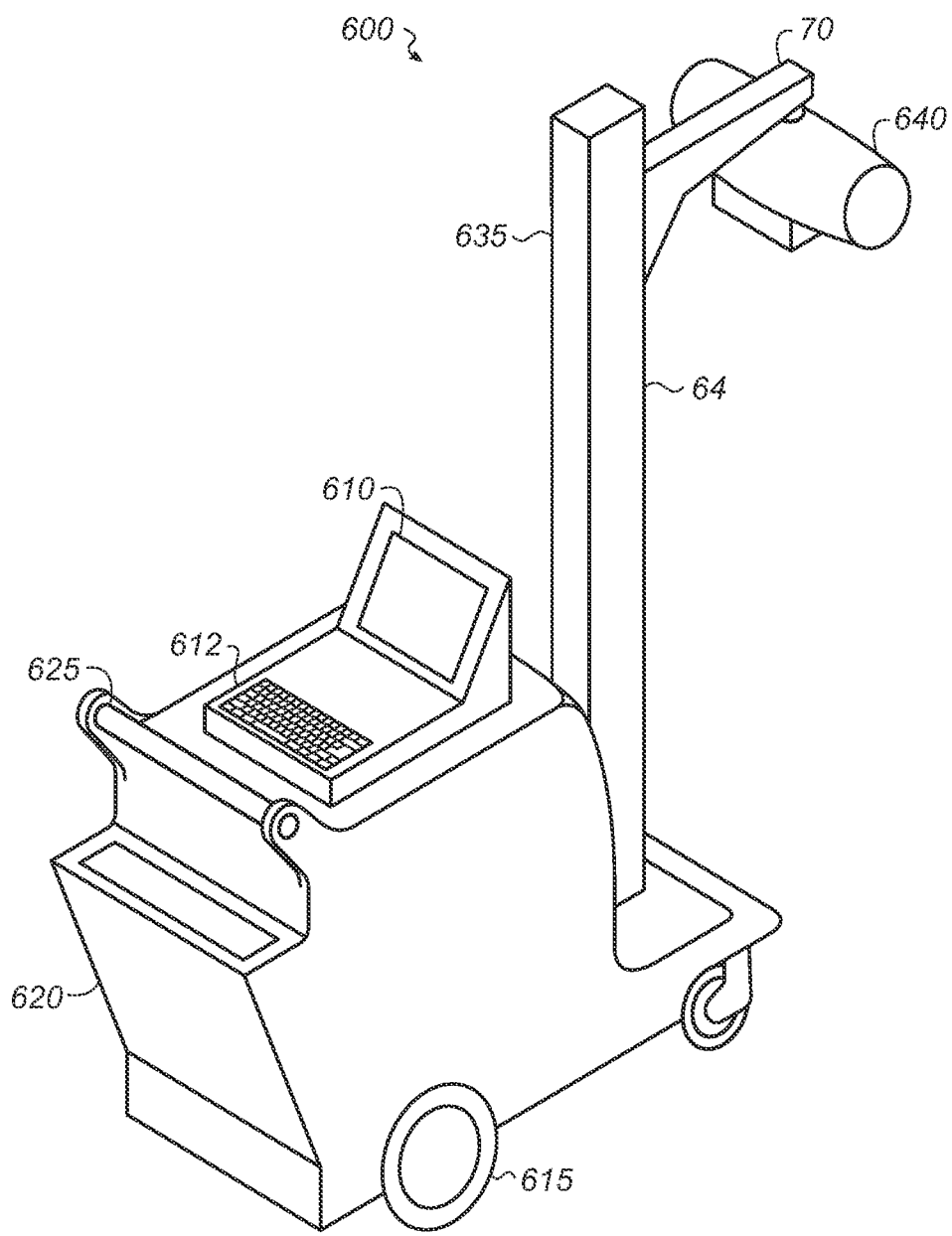
FIG. 1 shows a perspective view of a conventional mobile radiography unit using a fixed length vertical column for positioning the x-ray source.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Figure 2:
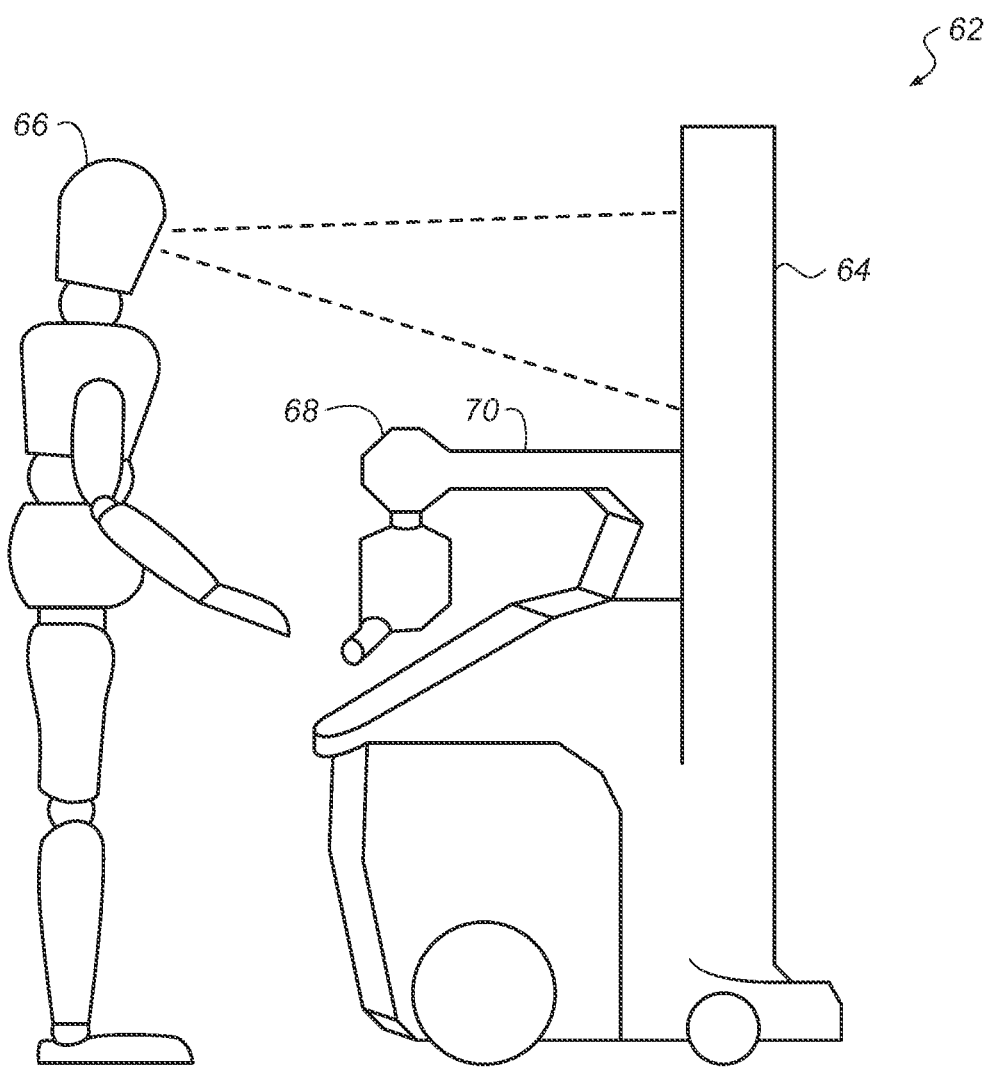
FIG. 2 shows a side view of a conventional mobile radiography unit with a fixed vertical column for positioning the x-ray source.

Apparatus and methods of the present invention address the need for a radiography unit that can be readily wheeled from one place to another within a treatment facility, without the physical or visual obstruction that is common to many types of conventional mobile radiography equipment that use a vertical column. As noted previously, the x-ray source of such a system must allow elevation over a wide vertical range of motion, from heights near or above shoulder level for adults to very low elevations near the ankle or foot. One way to achieve this range of movement is the use of a jointed support member, as described previously. A somewhat simpler mechanical design is the use of a stationary vertical column as was shown in FIGS. 1 and 2, with the x-ray source mounted on a boom that extends outward horizontally from the column and travels vertically up and down the column. Two degrees of freedom are needed for boom 70 relative to the vertical column: translation along the vertical direction and rotation about the vertical axis. Boom 70 typically also extends to a variable horizontal length in a direction relative to the vertical axis, although it should be noted that a boom of fixed length could be used in a mobile radiography apparatus of the present invention.

Figure 3:
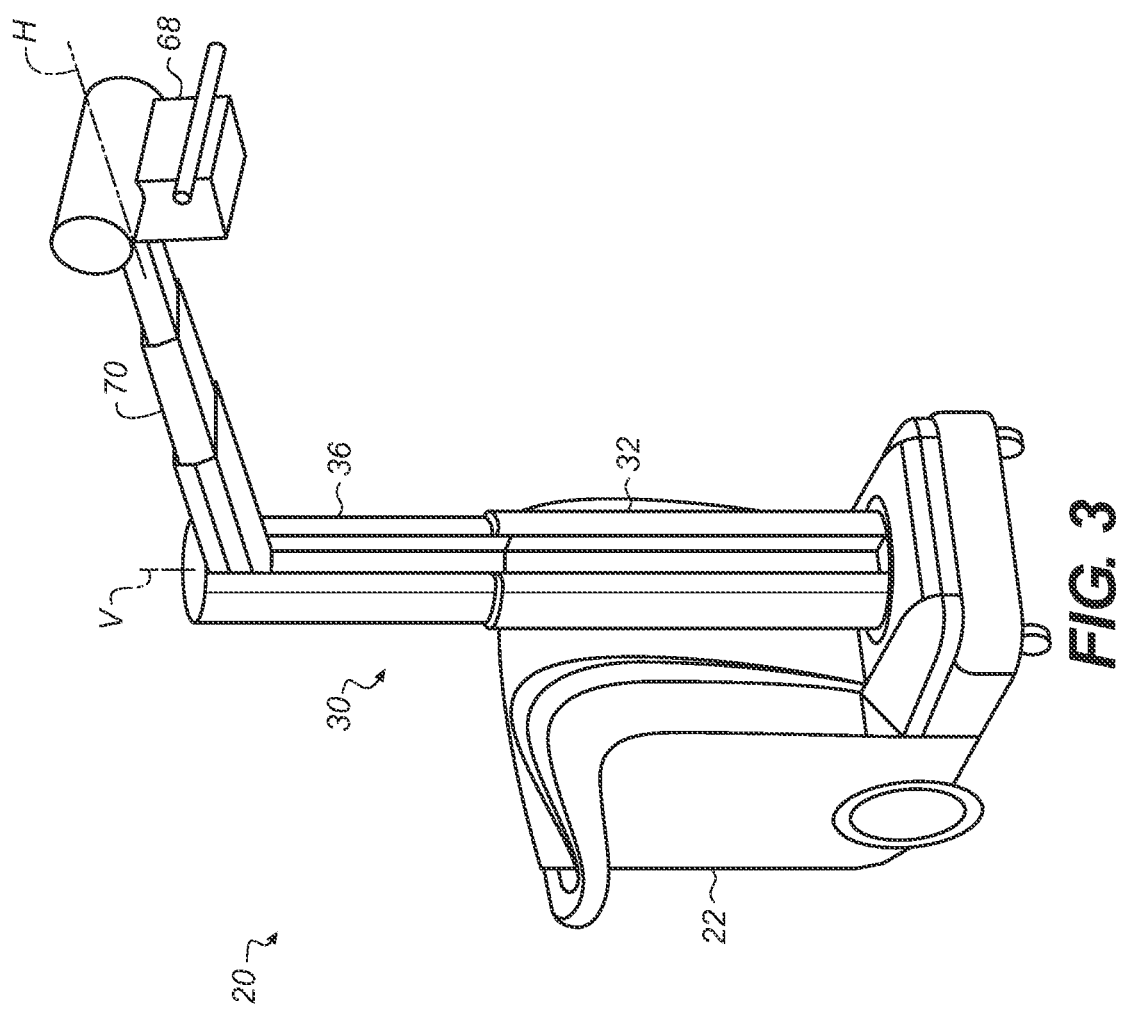
FIG. 3 shows a perspective view of a mobile radiography unit with a sectioned vertical column according to one embodiment of the present invention.
Figure 4:
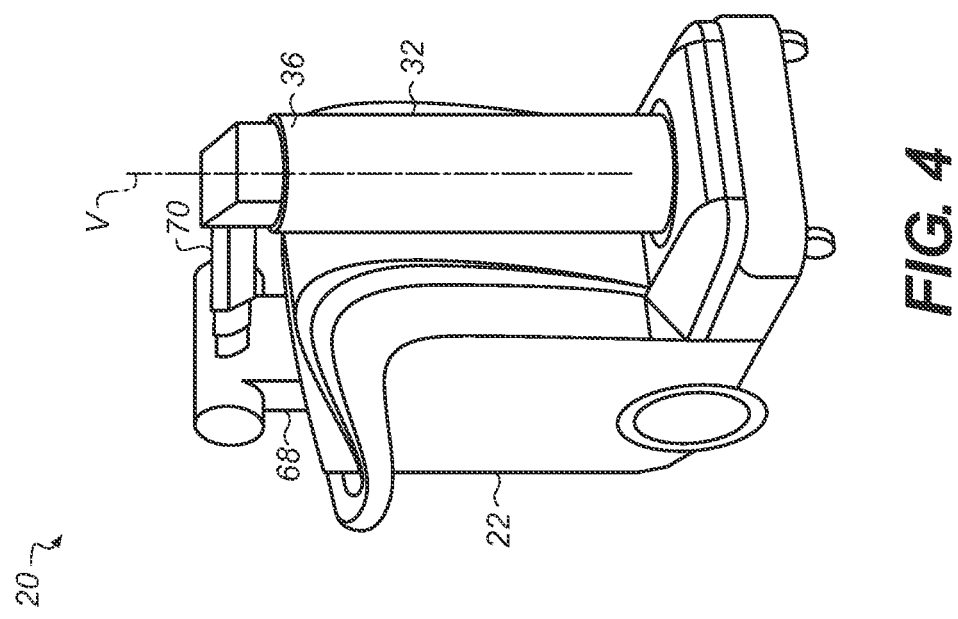
FIG. 4 shows a perspective view of a mobile radiography unit with a sectioned vertical column configured for travel.
Figure 5:
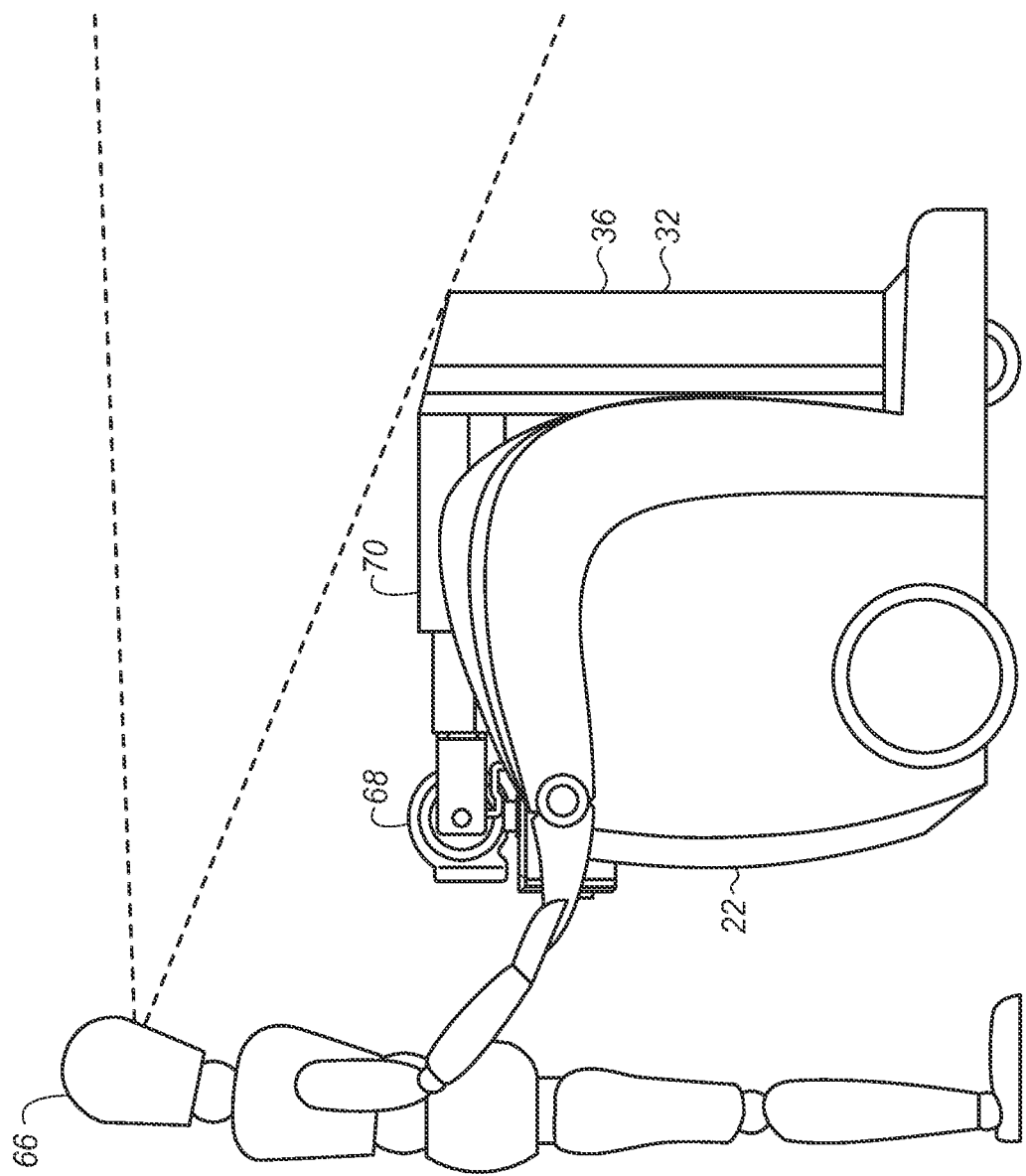
FIG. 5 shows a side view of a mobile radiography unit with a sectioned vertical column according to one embodiment of the present invention.

The perspective view of FIG. 3 shows a mobile radiography unit 20 that has boom 70 coupled to a sectioned vertical column 30 according to one embodiment. FIG. 3 shows unit 20 with x-ray source 68 in position for imaging, extended outward and supported on boom 70, along a horizontal axis H that is perpendicular to the vertical axis V. FIG. 4 shows unit 20 in an alternate arrangement, configured for travel, with sectioned vertical column 30 collapsed and with x-ray source 68 nestled against a top surface of the unit. The side view of FIG. 5 shows unit 20 configured for travel and shows how, using the collapsed column, technician visibility is improved over the conventional fixed vertical column arrangement shown previously in FIGS. 1 and 2.

In each of the embodiments shown in FIGS. 3-13, mobile radiography unit 20 has a wheeled transport frame 22 and has display and control panel components needed for operation, as was described previously with reference to FIG. 1. Sectioned vertical column 30, mounted on frame 22, defines a vertical axis V and has a base section 32 that seats against frame 22 and has a first vertical position relative to axis V, a fixed vertical position in one embodiment. One or more movable sections 34 and 36 are translatable to extend along the vertical axis V, so that boom 70 can be set to a suitable height over a range of possible height settings. In each embodiment, x-ray source 68 can be set to variable vertical and horizontal positions as well as to a range of angular positions about the vertical axis V.

In the embodiment shown in FIGS. 6 through 10, sectioned vertical column 30 has two movable sections, a first, top movable section labeled 36 and a second, middle movable section 34. Sections 34 and 36 are movable in telescoping fashion with respect to stationary base section 32. Boom 70 extends outward from sectioned vertical column 30 and can be rotated into position about vertical axis V. Rotation about axis V can be achieved in a number of ways. In the embodiments shown in FIGS. 6 through 10, sectioned vertical column 30 itself rotates in relation to its transport frame 22. FIG. 11 shows, again from a side view, an alternate embodiment in which column 30 itself does not rotate, but boom 70, mounted at the top of outermost movable section 36, pivots about vertical axis V by rotating about vertical section 36. In yet another embodiment, only the outermost movable section 36, with its attached boom 70, rotates. In each of these embodiments, both rotation about vertical axis V and vertical displacement along the vertical axis can be performed simultaneously.

Figure 6:
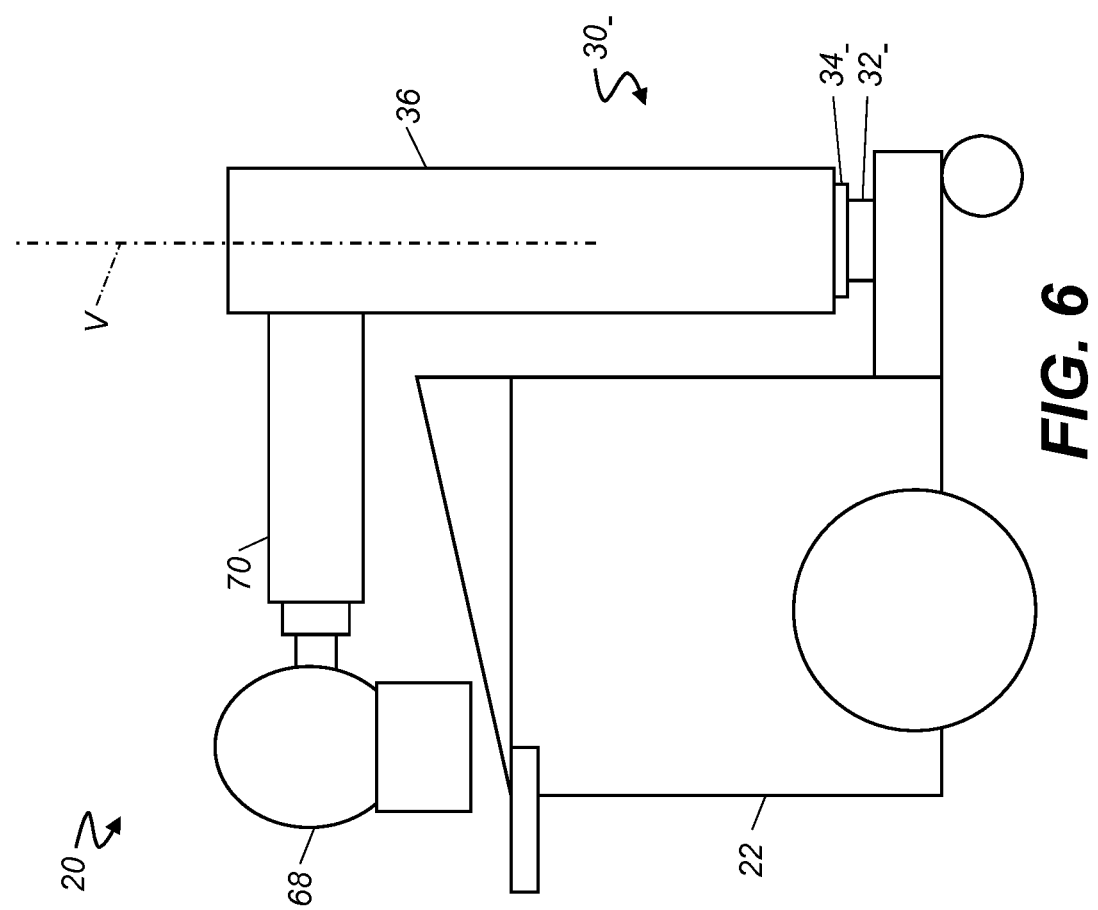
FIG. 6 is a side view showing a mobile radiography unit having a sectioned vertical column and configured for transport.
Figure 7:
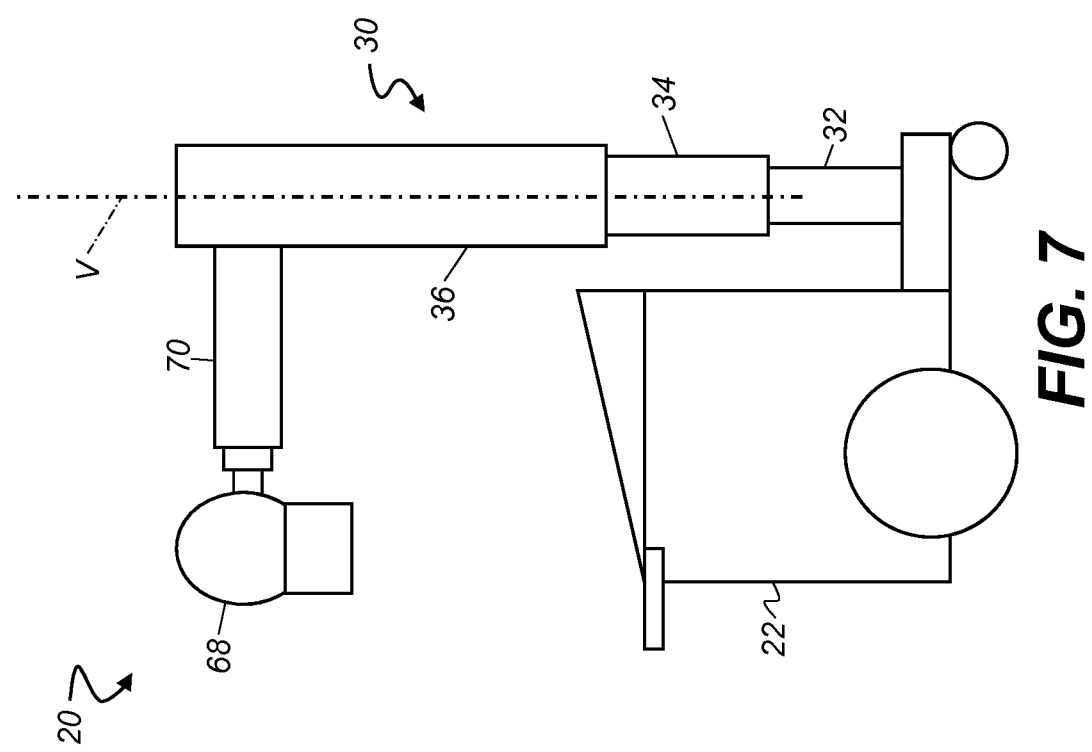
FIG. 7 is a side view showing a mobile radiography unit having a sectioned vertical column and being set up for imaging.
Figure 8:
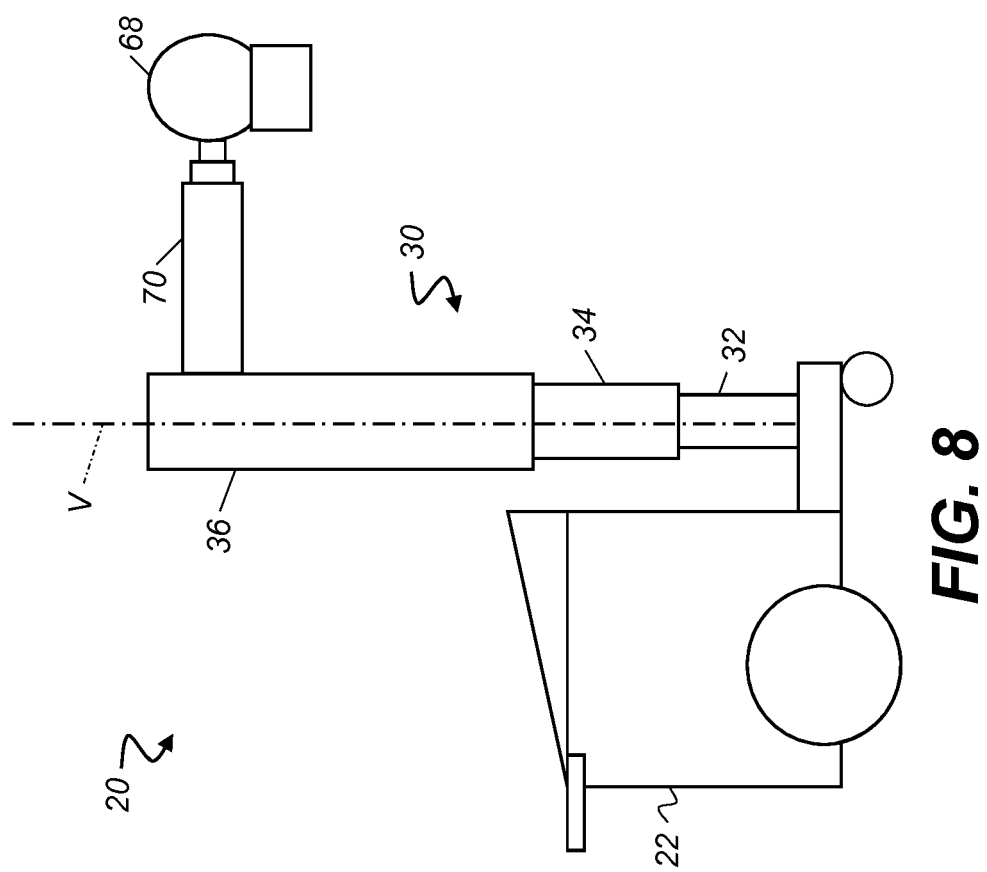
FIG. 8 is a side view showing a mobile radiography unit having a sectioned vertical column that is fully extended for patient imaging.
Figure 9:
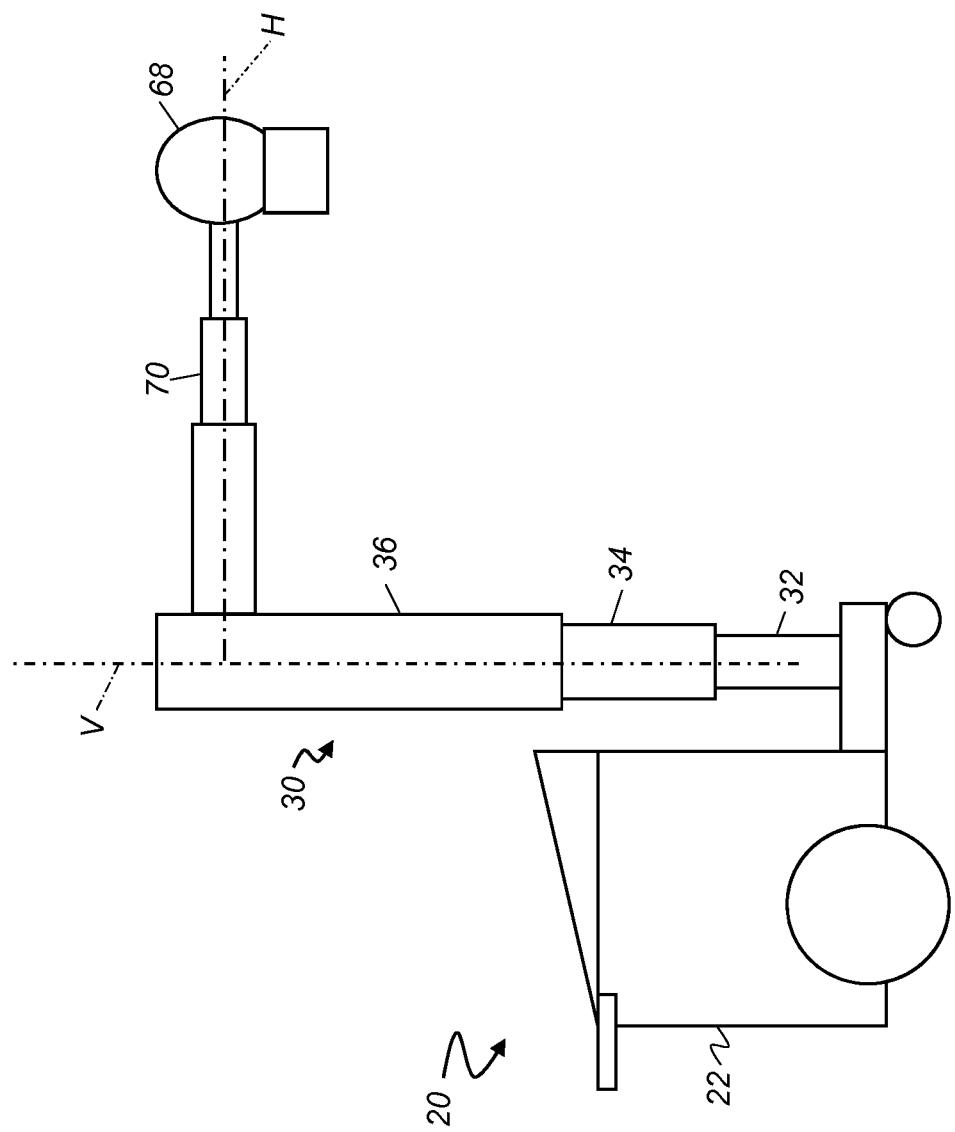
FIG. 9 is a side view showing a mobile radiogaphy unit having a sectioned vertical column that is fully extended for patient imaging with an extended boom fig the x-ray source.

In the travel configuration of FIG. 6, sectioned vertical column 30 is collapsed and boom 70 is rotated inward in order to seat x-ray source 68 in a stable position for movement, such as for wheeling from one patient area to another. FIG. 7 shows initial elevation of sectioned vertical column 30 upward from its travel position, readying the unit for deployment. FIG. 8 shows vertical column 30 fully extended, with boom 70 facing outward and with movable sections 34 and 36 at their extreme end of travel. FIG. 9 shows x-ray boom 70 extended orthogonally outward from sectioned vertical column 30 along horizontal axis H, ready for imaging in this position.

Figure 10:
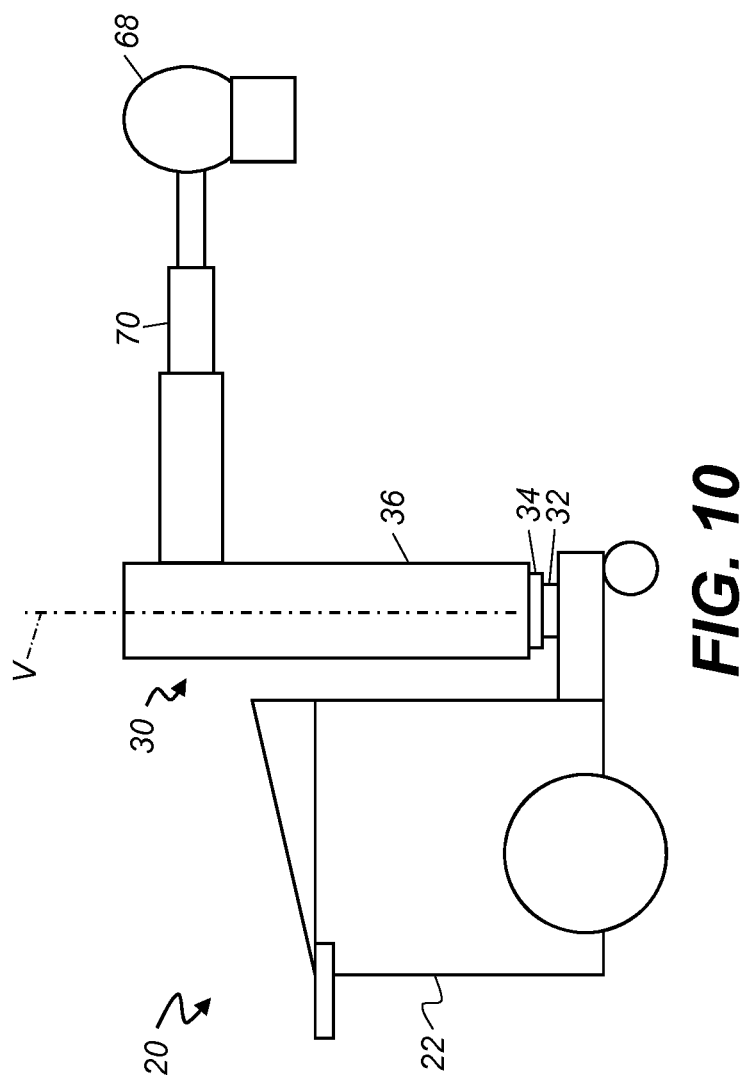
FIG. 10 is a side view showing a mobile radiography unit having a sectioned vertical column that is collapsed for patient imaging of lower extremities.
Figure 11:
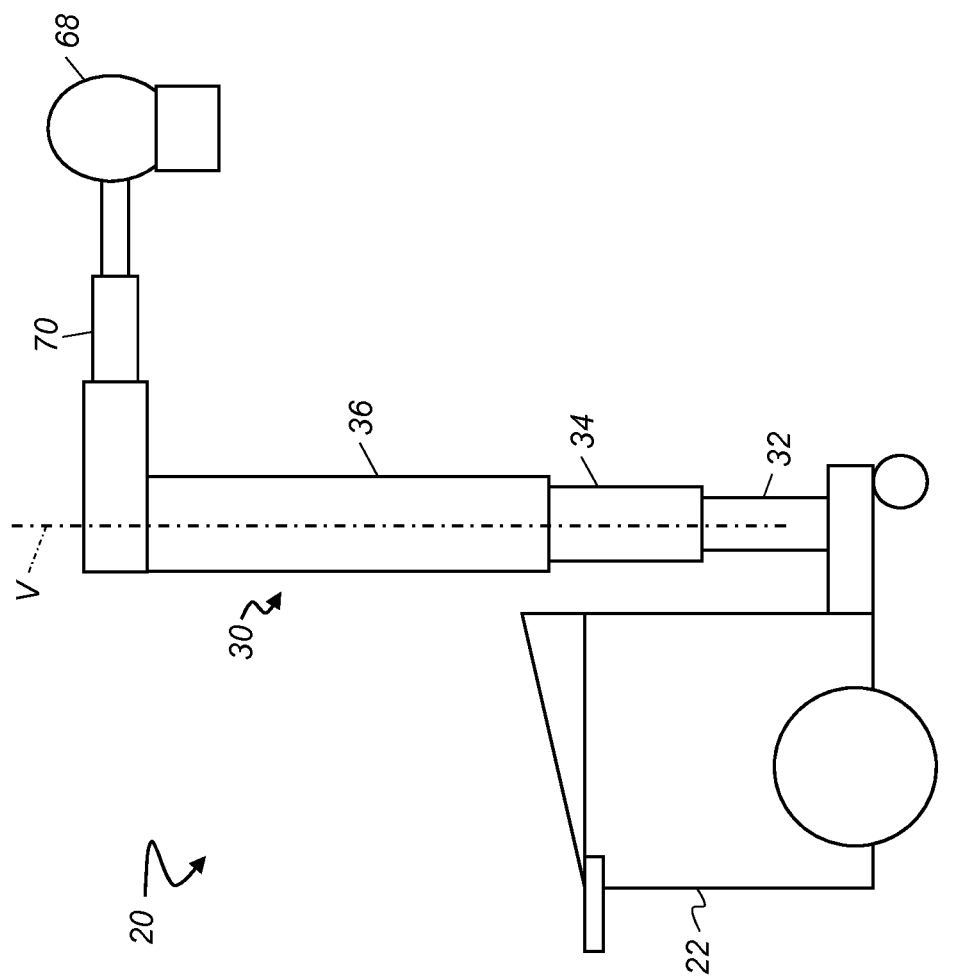
FIG. 11 is a side view showing an alternate embodiment in which the x-ray boom rotates about the top of the vertical column.

With the configuration shown in FIGS. 3-11, the lowest height position for the x-ray source is determined by the length of the outermost movable section 36 and by the position of boom 70 along that length. By way of example, FIG. 10 shows sectioned vertical column 30 in a nearly fully collapsed position, setting x-ray source 68 at low height, near the bottom of its vertical travel range. Using this type of design, the low end of vertical travel is constrained by the position of boom 70 on the outermost section and the length of this section. A lower height can be achieved by increasing the number of movable sections and shortening their respective lengths. It can be appreciated that, beyond a certain number of movable sections, the increased part count and corresponding mechanical complexity can impose some bounds on the practicality of this type of solution for expanding the vertical travel distance to below a certain height.

It is beneficial to allow the fullest possible range of vertical heights for the x-ray source in a portable system, from above shoulder height of the imaging technician to relatively low elevations, such as might be beneficial for imaging the foot or ankle of a patient. As has been shown, this desired height range presents a problem for telescoped column designs. When a telescoped column is fully collapsed, as described with reference to FIG. 10, boom 70, attached to the outermost movable column, can no longer be moved downward. This movement limitation can make the telescoping arrangement less desirable for portable radiography systems.

Embodiments of the present invention address this difficulty by using a boom transport mechanism that cooperates mechanically with a telescoping, sectioned vertical column to allow displacement of the x-ray boom over a wide range of height settings. Advantageously, the operator can easily adjust x-ray boom height, with the weight of column and boom components mechanically balanced so that a substantially uniform amount of effort is needed for height adjustment to any level within the height range.

Figure 12:
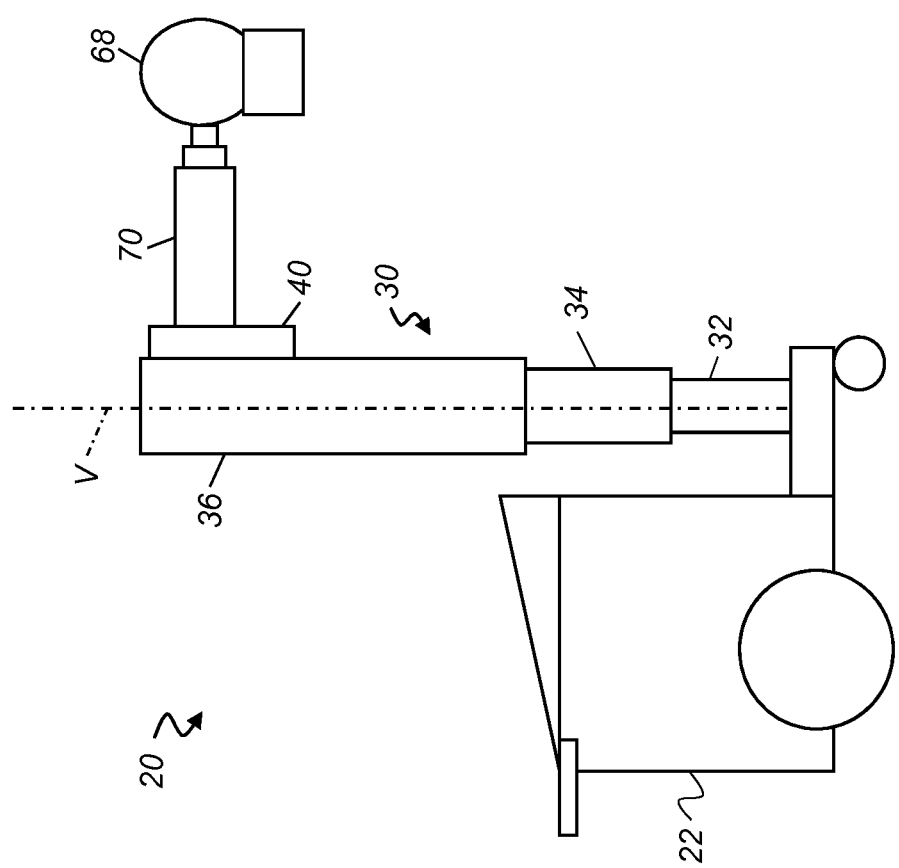
FIG. 12 is a side view that shows an alternate embodiment having a boom transport mechanism for vertical motion of the boom along the length of the uppermost vertical section.
Figure 13:
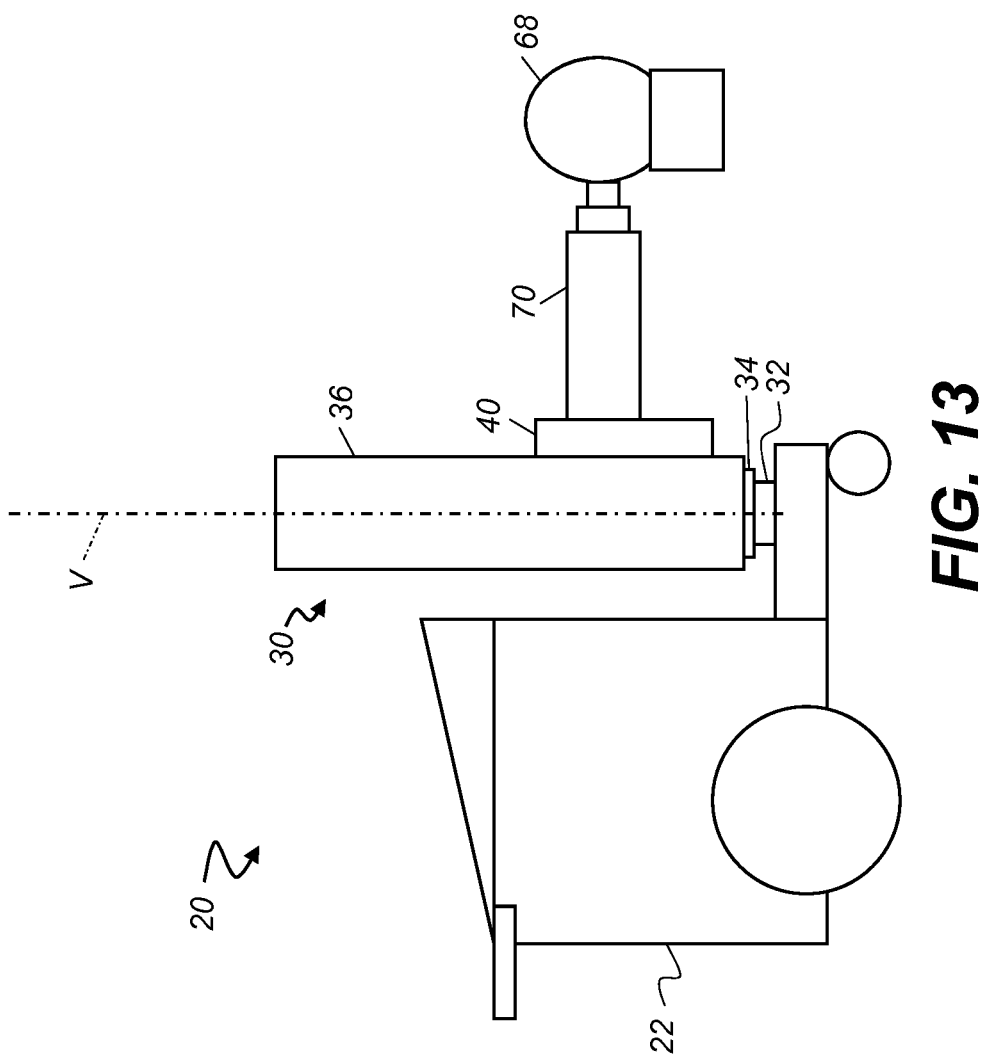
FIG. 13 is a side view that shows how the boom transport mechanism allows lowering of the boom for imaging at low heights.

The side views of FIGS. 12 and 13 show an alternate embodiment of mobile radiography unit 20 in which a boom transport mechanism 40 is mounted on outermost movable section 36 and is actuable to provide the added vertical range needed for imaging with source 68 at a low elevation below the range that is typically feasible with sectioned vertical column 30 fully collapsed when using the embodiment shown in FIG. 10. Boom transport mechanism 40 allows a second mode of vertical displacement for boom 70, so that not only is boom 70 mounted on a vertically collapsible column, but its vertical travel is further permitted for a distance along the length of the outermost movable section.

An important design aspect for usability of mobile radiography unit 20 is the ease of movement that is needed for positioning x-ray source 68 in the proper position relative to the patient and to the x-ray detector panel. This is a complex mechanical problem due, in part, to the weight of the x-ray tube and its collimator, which can exceed 100 pounds in some systems. The operator should be able to readily move x-ray source 68 to the needed vertical and horizontal position without undue exertion. In addition, the amount of effort needed to adjust the elevation of x-ray source 68 should be balanced over its full range of vertical displacement, so that substantially no additional effort is needed to adjust the height from one level to another.

Figure 14:
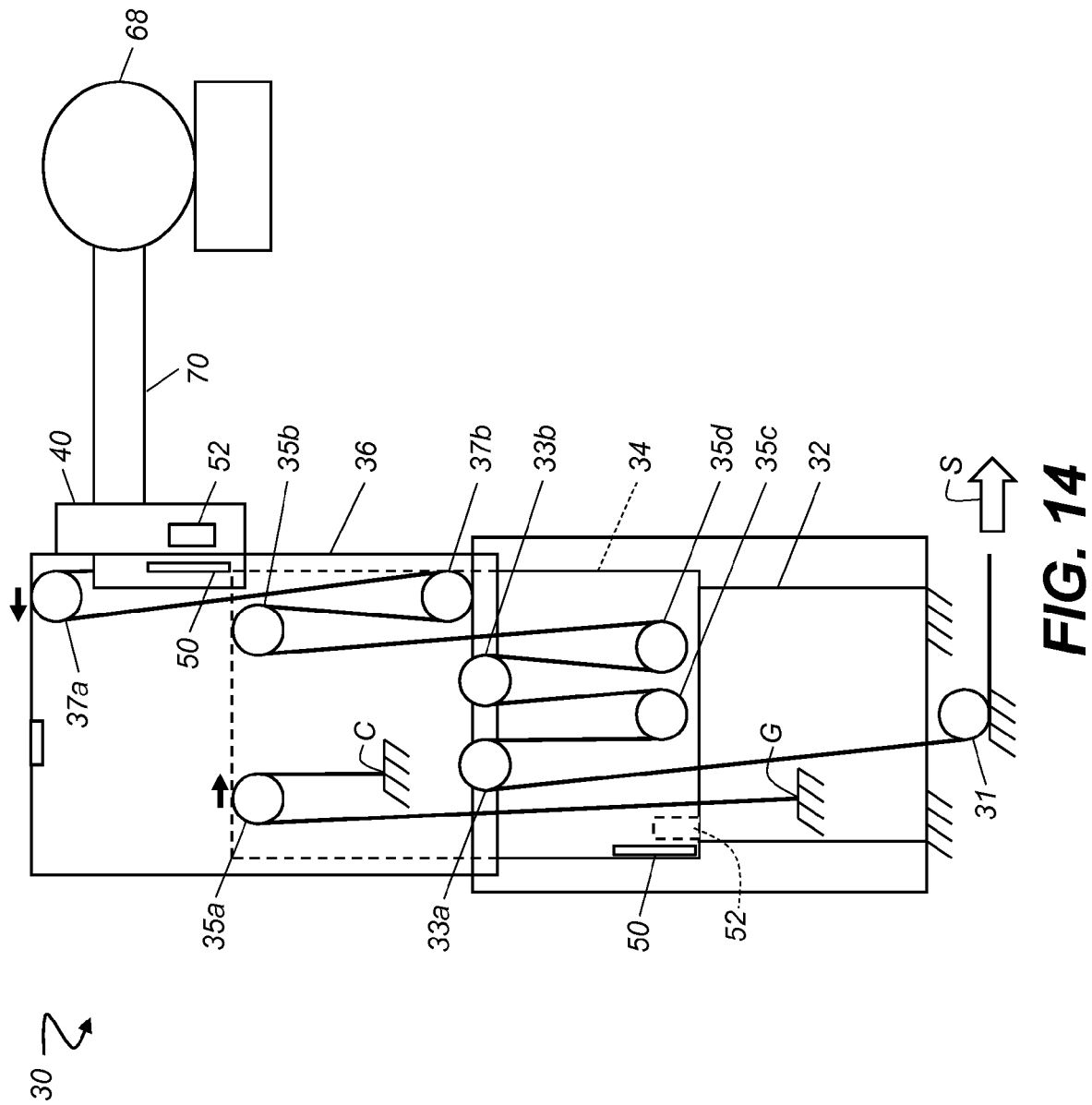
FIG. 14 is a sectioned side view showing an arrangement of pulleys, loads, and counterweights for providing ease of movement of the sectioned vertical column.
Figure 15:
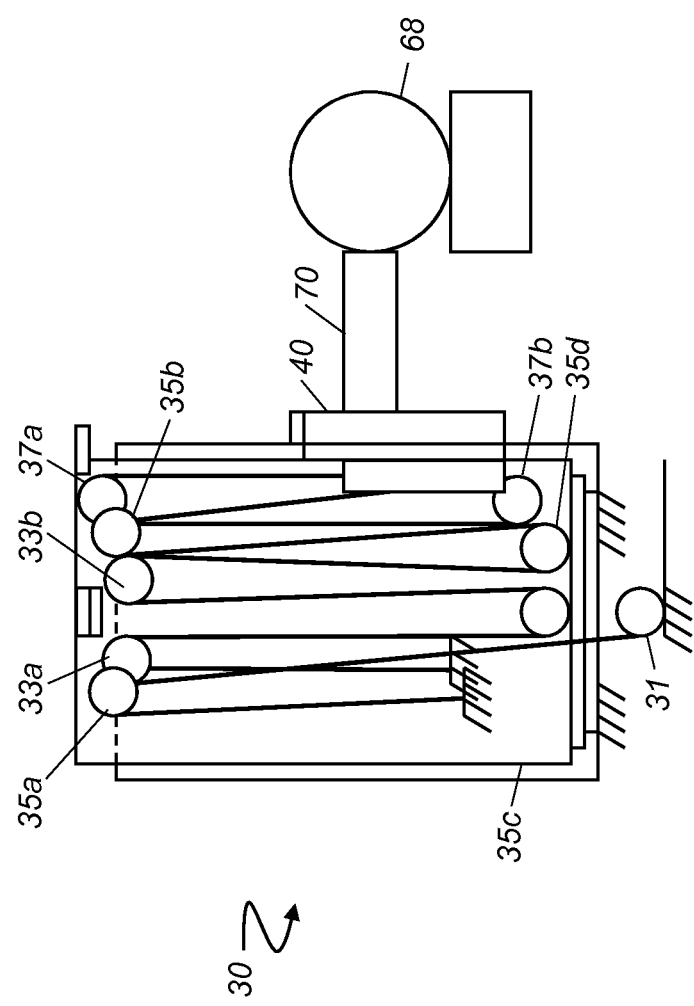
FIG. 15 is a sectioned side view showing the column arrangement of FIG. 14 with the column collapsed to its minimum height.

Cross-sectional views of FIGS. 14 and 15 show how the amount of work needed for vertical adjustment is equalized over the range of vertical displacement in the FIGS. 12 and 13 embodiment of sectioned vertical column 30 that uses boom transport mechanism 40. FIG. 14 shows the pulley arrangement when column 30 is extended. FIG. 15 shows the pulley arrangement when column 30 is fully collapsed. Differences in shading treatment help to indicate which pulleys are located on which section. Pulleys 33*a* and 33*b* are within base section 32. Pulleys 35*a*, 35*b*, 35*c*, and 35*d* are within intermediate movable section 34. Pulleys 37*a* and 37*b* are part of outermost or upper movable section 36.

In order to provide balanced weighting of sectioned vertical column 30, both upper movable section 36 and intermediate movable section 34 move at the same time. This arrangement eliminates the need to handle the weight transition that might otherwise occur at the end of travel of one or the other section if sections were separately movable. Distance equalization for this behavior is provided by pulley 35*a*, part of intermediate movable section 34. This pulley arrangement is mechanically grounded to upper movable section 36 at C and to base section 32 at G.

Cooperating with the distance equalization function of pulley 35*a*, the combined interaction of pulleys 33*a*, 35*c*, 33*b*, 35*d*, 35*b*, 37*b*, and 37*a*, with coupling to boom transport mechanism 40, form a block-and-tackle assembly that effectively doubles the force exerted for extending or contracting vertical column 30 over its height range. This arrangement is shown in FIG. 14. A spring force S, transmitted using pulley 31, provides a uniform loading that provides a constant counterbalance force for vertical column 30 movement. In one embodiment, spring force S loading is provided by a spring. Alternate embodiments provide counterbalance loading using a weight or actuator such as a motor, for example.

The sectioned view of FIG. 15 shows the arrangement with column 30 in a collapsed position. An automatic brake mechanism, or, alternately, a mechanical stop, constrains movement of movable sections 34 and 36, so that these sections remain in fixed vertical positions. Because there is no countering force exerted from distance equalization components in this position, there is no mechanical advantage to the action of pulleys 33a, 35c, 33b, 35d, 35b, 37b, and 37a with column 30 collapsed as shown. This system of pulleys then allows movement of boom transport mechanism 40 vertically along outermost section 36.

The embodiment of column 30 described with reference to FIGS. 14 and 15 allows movement with application of uniform force over the vertical travel distance of boom 70 by balancing the weight of the movable components according to the forces exerted and mechanical advantage of its pulley configuration. Thus, for example, the weight W1 of boom 70 with its included components is equal to the sum of half the weight W3 of middle section 34 plus the weight W2 of upper section 36. It can be appreciated that other arrangements of component weights and pulley configurations are possible, as well as mechanical configurations using counterweights or various types of electromechanical or hydraulic actuators, fix example.

Referring again to FIG. 14, one or more arrangements of a magnetic brake 52 and corresponding plate 50 provide mechanisms for braking the vertical motion of components of sectioned vertical column 30. In one embodiment, brakes are "on" or engaged in lock position by default, providing braking force until they are energized or actuated. When energized or actuated, brakes unlock or go "off" to allow movement. In the lower brake shown, plate 50 is coupled to movable section 34 while brake 52 is coupled to base section 32. A second plate 50 is coupled to movable section 36 with its corresponding brake 52 coupled to boom transport mechanism 40. It can be appreciated that other braking arrangements are possible, including configurations that reverse the braking logic from that just described, so that brakes are off when de-energized and on or engaged when energized. Additional braking is provided by an interlock that constrains the speed of wheeled transport of the mobile radiography apparatus when the sectioned vertical column is in an extended (non-travel) position.

Figure 16:
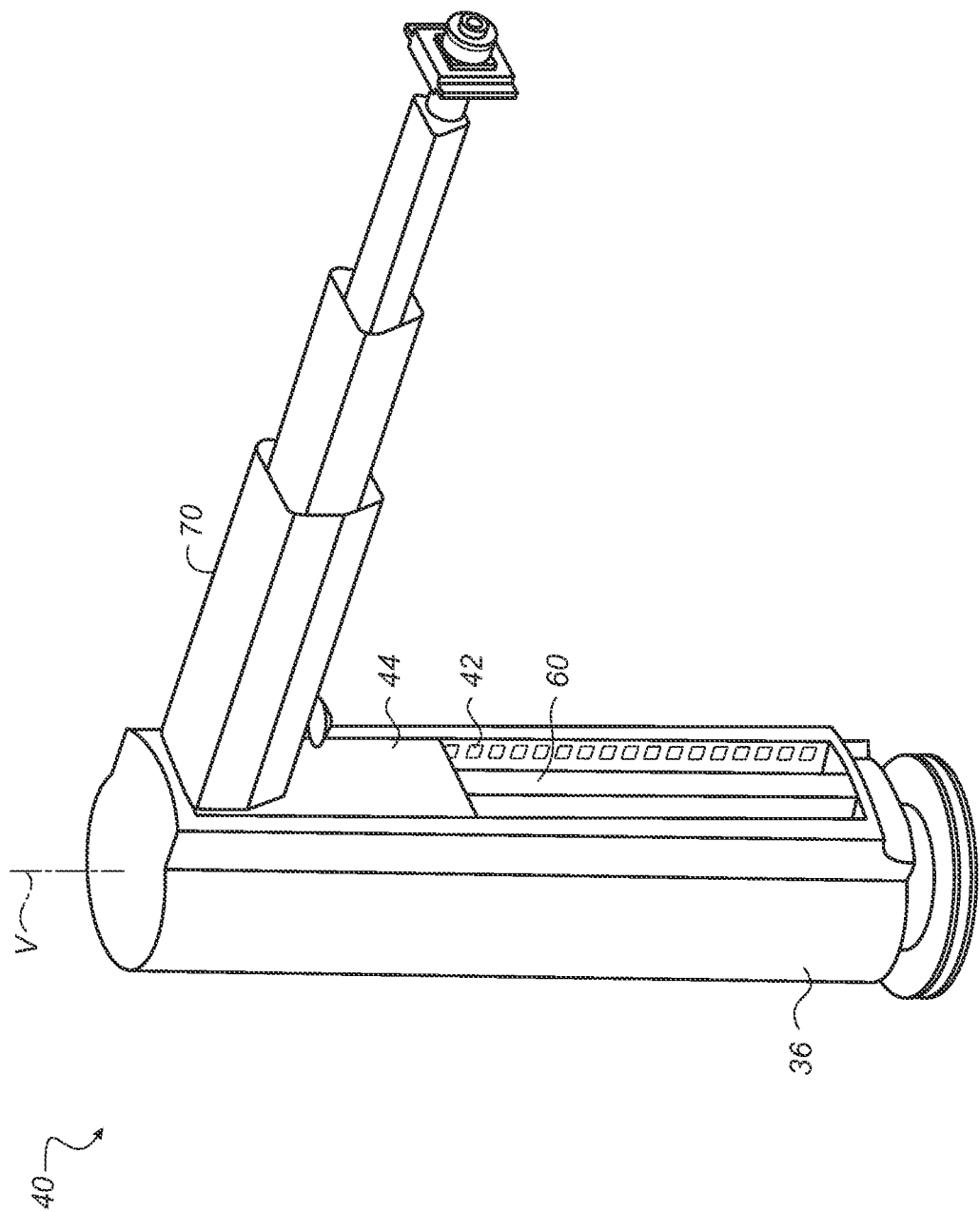
FIG. 16 is a perspective view showing the boom transport on the upper section of the collapsible column, with the transport in an upper position.

The perspective views of FIGS. 16, 17, and 18 show boom transport mechanism 40 and carriage mechanism 44 in different vertical positions along upper section 36. In the figure, boom transport mechanism 40 is coupled to section 36 by wheeled carriage mechanism 44 that is movable within a track.

FIGS. 19A and 19B show carriage mechanism 44 of the boom transport mechanism 40 in one embodiment. Boom transport mechanism 40, shown in more detail in top and side views of FIGS. 19A and 19B, respectively, has a series of wheels 54 that rotate within a track 42 to provide vertical displacement. Four wheels are used for this function in the embodiment shown in FIGS. 19A and 19B. Two additional pairs of wheels 58 rotate in an orthogonal direction against a centering block 60 in order to constrain unwanted side-to-side movement of boom 70 relative to the vertical axis. It can be appreciated that alternative embodiments can be used for boom transport mechanism movement, including the use of one or more linear bearings, for example.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

What is claimed is:

1. A mobile radiography apparatus comprising:
   a wheeled transport frame;
   a sectioned vertical column mounted on the frame and defining a vertical axis and comprising,
   a base section having a first vertical position relative to the vertical axis,
   at least a first movable section that is translatable to a variable vertical position along the vertical axis,
   at least one middle section that is between the base section and the first movable section, wherein the at least one middle section is translatable to a variable vertical position along the vertical axis, and
   a first plurality of pulleys internal to the base section, a second plurality of pulleys internal to the middle section, and a third plurality of pulleys internal to the first movable section; and
   a boom apparatus to support an x-ray source;
   a boom transport mechanism coupled to the first movable section or the middle section, wherein the boom transport mechanism is actuable to provide vertical movement along at least a portion of the first movable section or the middle section, wherein the boom apparatus is coupled to the boom transport mechanism for positioning of the x-ray source along the vertical axis and extends outward with respect to the sectioned vertical column for positioning of the x-ray source in a direction that is orthogonal to the vertical axis, and
   where a mechanical advantage of the pulley configuration in the sectioned vertical column balance a weight of movable components including the first movable section, the middle section, the boom apparatus, and the boom transport mechanism to allow a substantially uniform force to adjust a height of the movable components within a height range of the movable components relative to the vertical axis.

2. The apparatus of claim 1 further comprising a brake mechanism that, when actuated, prevents vertical movement of the at least first movable section.

3. The apparatus of claim 1 further comprising an interlock that constrains the speed of wheeled transport of the mobile radiography apparatus when the sectioned vertical column is in an extended position.

4. The apparatus of claim 1 wherein the sectioned vertical column is rotatable about the vertical axis.

5. The apparatus of claim 1 wherein the first movable section is rotatable about the vertical axis.

6. The apparatus of claim 1 wherein the boom apparatus rotates about the first movable section.

7. The apparatus of claim 1 providing simultaneous vertical and rotational movement of the boom apparatus relative to the vertical axis.

8. A mobile radiography apparatus comprising:
   a wheeled transport frame;
   a sectioned vertical column mounted on the frame and defining a vertical axis and comprising a base section having a fixed vertical position relative to the vertical axis, at least a first movable section that is translatable to a variable vertical position along the vertical axis, and a mechanical interaction assembly in the base section and the first movable section to provide a mechanical advantage to force applied to move the sectioned vertical column;
   a boom transport mechanism on the first movable section, wherein the boom transport mechanism is actuable to provide vertical movement along at least a portion of the first movable section;
   a boom apparatus coupled to the boom transport mechanism and extending outward with respect to the sectioned vertical column; and
   an x-ray source coupled to the boom apparatus for positioning using the boom transport mechanism, where the mechanical interaction assembly is configured to provide the mechanical advantage to balance a weight of movable components including the first movable section, the boom apparatus, and the boom transport mechanism to allow a substantially uniform force to adjust a height of the x-ray source within a height range of the x-ray source provided by the mobile radiography apparatus.

9. The apparatus of claim 8 further comprising a brake mechanism that prevents vertical movement of the at least first movable section and that actuates automatically when the sectioned vertical column is in a collapsed position.

10. The apparatus of claim 8 wherein the sectioned vertical column further comprises at least one middle section that is between the base section and the first movable section, wherein the at least one middle section is translatable to a variable vertical position along the vertical axis.

11. The apparatus of claim 10 further comprising a plurality of pulleys internal to the column and cooperating to provide simultaneous vertical movement of the first movable section and the at least one middle section.

12. The apparatus of claim 11 providing simultaneous vertical and rotational movement of the boom apparatus relative to the vertical axis.

13. The apparatus of claim 11 further comprising a spring providing a counterbalance force for the plurality of pulleys.

14. The apparatus of claim 8 further comprising a brake element that is disposed to constrain vertical movement of the first movable section when the sectioned vertical column is in a collapsed position.

15. The apparatus of claim 8 wherein the boom transport mechanism is coupled to the first movable section by a wheeled carriage that is movable within a track.

16. The apparatus of claim 8 further comprising an interlock that constrains the speed of wheeled transport of the mobile radiography apparatus when the sectioned vertical column is in an extended position.

17. The apparatus of claim 8 wherein the sectioned vertical column is rotatable about the vertical axis.

18. A method for mounting an x-ray source for use at variable heights for a mobile radiography apparatus, comprising:
   providing a sectioned vertical column that comprises a base section having a fixed vertical position relative to a vertical axis, at least a first movable section that is translatable to a variable vertical position along the vertical axis, and a mechanical interaction assembly in the base section and the first movable section to provide a mechanical advantage to force applied to move the sectioned vertical column;
   coupling a boom transport mechanism onto the first movable section, wherein the boom transport mechanism is actuable to provide vertical movement along at least a portion of the first movable section; and
   coupling a boom apparatus to the boom transport mechanism, the boom transport mechanism having an x-ray source for positioning at a desired height,
   where the mechanical interaction assembly is configured to provide the mechanical advantage to balance a weight of movable components including the first movable section, the boom apparatus, and the boom transport mechanism to allow a substantially uniform force to adjust a height of the x-ray source within a height range of the x-ray source provided by the mobile radiography apparatus.

19. The method of claim 18 wherein the sectioned vertical column further comprises at least one middle section that is between the base section and the first movable section, wherein the at least one middle section is translatable to a variable vertical position along the vertical axis.

20. The method of claim 19 further comprising a plurality of pulleys internal to the column and cooperating to provide simultaneous movement of the first movable section and the at least one middle section.

21. The method of claim 20 further comprising a spring providing a counterbalance force for the plurality of pulleys.

\* \* \* \* \*